Figure 1:
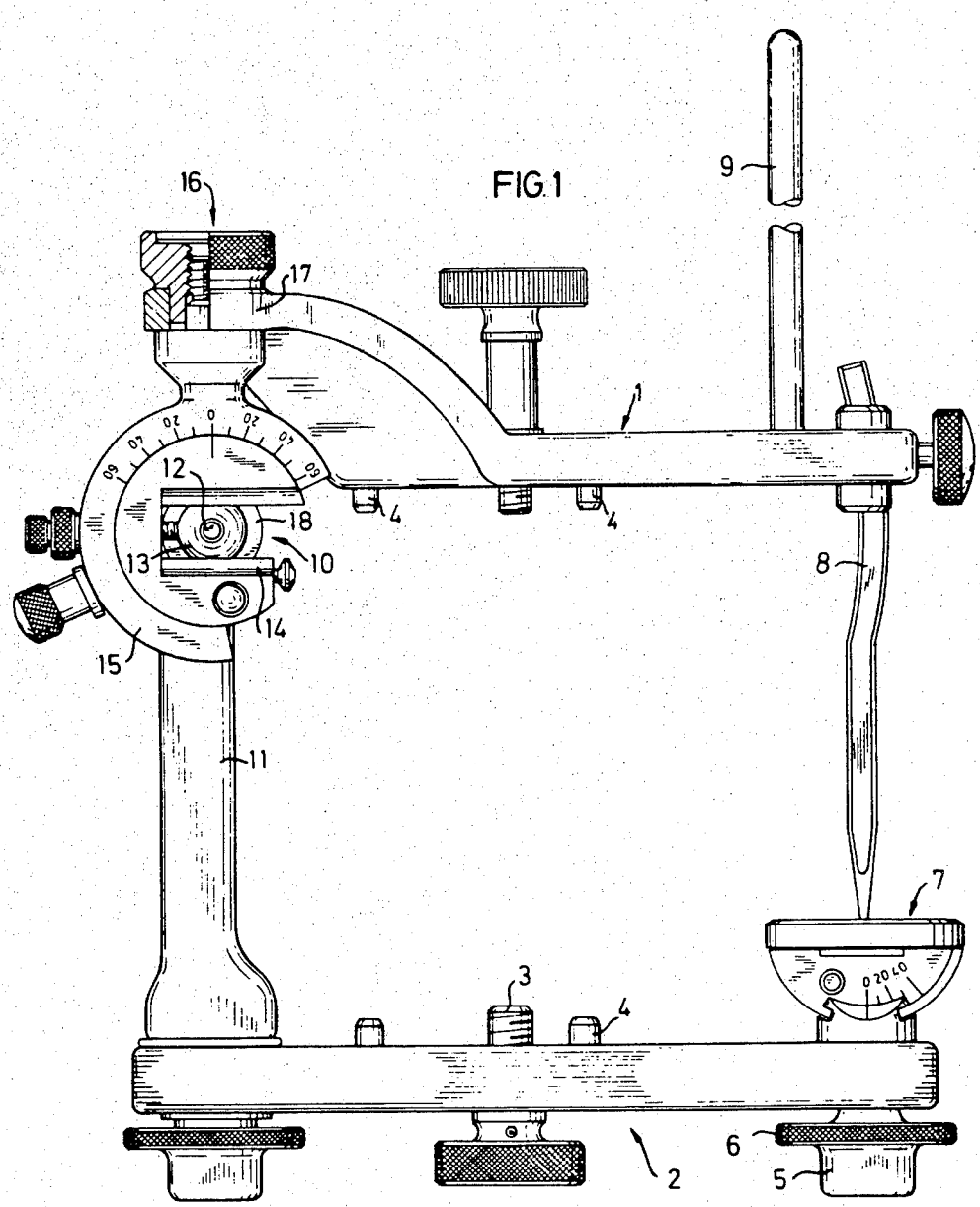

United States Patent [19]

Edwardson

[11] 4,290,754
[45] Sep. 22, 1981

[54] ARTICULATOR FOR USE IN THE MAKING OF DENTURES OR PARTS THEREOF

[75] Inventor: Svante R. Edwardson, Solna, Sweden

[73] Assignee: AB Dentatus, Hagersten, Sweden

[21] Appl. No.: 120,886

[22] Filed: Feb. 12, 1980

[51] Int. Cl.³ .............................................. A61C 11/00
[52] U.S. Cl. ......................................... 433/56; 433/57
[58] Field of Search .............................. 433/59, 64, 56

[56] References Cited

U.S. PATENT DOCUMENTS 2,600,899  6/1952  McClain .............................. 433/64
2,748,481  6/1956  Gluerk ................................ 433/56

Primary Examiner—Robert Peshock
Attorney, Agent, or Firm—Young & Thompson

[57] ABSTRACT

An articulator for use in making dentures or parts thereof wherein two principal members, pivotable relative to each other by means of conventional condylar mechanisms, have anchoring means for teeth models required for making the dentures. In order for one principal member to carry the other, it has a single, slender arm or post which at its end towards the other member carries the condylar shafts of the condylar mechanisms, with the condylar balls displaceable on said shafts, while the other principal member carries the condylar tracks.

5 Claims, 3 Drawing Figures

ARTICULATOR FOR USE IN THE MAKING OF DENTURES OR PARTS THEREOF

The present invention relates to an articulator for use in making dentures or parts thereof, which comprises two principal members which are provided with anchoring means for carrying models of the upper and the lower rows of teeth, one of said members being pivotable in relation to the other by means of two condylar mechanisms which simulate the movements of the jaw joint.

By virtue of the fact that such articulators make it possible to anchor models of a patient's upper and lower sets of teeth and simulate the patient's bite and jaw movements, the teeth in the finished denture or denture portion can be made to interact in a satisfactory manner.

Since the adjustment and processing of the models in an articulator requires the greatest care and accuracy, it is important that they be as accessible as possible when mounted in the articulator. Even if the accessibility of the models is in this respect more or less acceptable in the type of known articulator in which the condylar tracks of the condylar mechanisms are carried at the upper end of two upright pillars, extending from the principal member forming the base or frame of the articulator, accessibility and visibility are greatly limited at certain critical angles in the known articulators, which are of the so-called arcone type, and have their condylar tracks mounted on the principal member of the articulator which is the upper member and is carried by the base or frame. In such articulators, the balls and shafts in the condylar mechanisms are carried by a number of pillars extending upwards from the base which greatly reduce access from several directions to the interior of the articulator where the work piece is located.

Therefore, the purpose of the invention is to suggest a new and improved articulator of the type described in the introduction, in which the adjustment possibilities have been increased and the access improved to such a high degree that the interior of this articulator is accessible from practically all sides.

This purpose has been achieved primarily by virtue of the fact that one principal member of an articulator made according to the invention carries the other, for which purpose said first-mentioned member has a single slender arm or post, which at its end towards the second principal member carries the condylar shafts, included in the condylar mechanisms which are known per se, with condylar balls which are displaceable on said shafts, while the second member carries the condylar tracks. In addition to increased accessibility and improved adjustment possibilities, especially the possibility of greater so-called Bennet deviation, i.e. oblique settings of the condylar tracks in relation to the condylar shafts, this embodiment according to the invention also provides a simplified and thus less expensive construction of the articulator.

In an embodiment of an articulator made according to the invention, which has been shown in practice to fulfill the requirements of such an articulator as well as being simple, stable and easily operated, the principal member provided with the single, slender post forms the base or stand of the articulator, while the principal member carried by said first member forms the upper member of the articulator, said upper member, with the aid of the condylar mechanisms, being pivotable in relation to the base or stand.

The single slender arm or post can be arranged in various manners for supporting the condylar shafts. In one embodiment for an articulator according to the invention, it can have two collinear, but oppositely directed, bores at its end towards the supported principal member. The condylar shafts are arranged to extend from these bores in either direction from the post. The condylar shafts can either be screwed in and locked or possibly inserted and locked in these bores. In another embodiment, which permits so-called complete adjustability of the condylar mechanisms, the condylar shafts can instead be arranged extending in either direction from the slender post, which for this purpose has a bore open on both sides of the post, at the end of the post towards the supported principal member. In this embodiment, the condylar shafts in the bore can be both individually and connectedly displaceable and lockable in the bore, with the portions inside the bore possibly being threaded into each other. This provides a very wide range of simple adjustment possibilities for the shafts which, as required, can thus be moved either individually in one direction or the other, or in opposite directions, or together in one direction or the other.

In order for an articulator made according to the invention to have so-called completely adjustable condylar mechanisms, the condylar tracks must, in addition to being pivotable and lockable around two mutually perpendicular axes, also be adjustable with regard to the spacing between them, by holders for the same being arranged on the supported principal member so as to be displaceable laterally in relation to said member and lockable in relation to said member.

The invention will be described in more detail in the following with reference to two examples shown in the accompanying drawings, of articulators made according to the invention.

Figure 2:
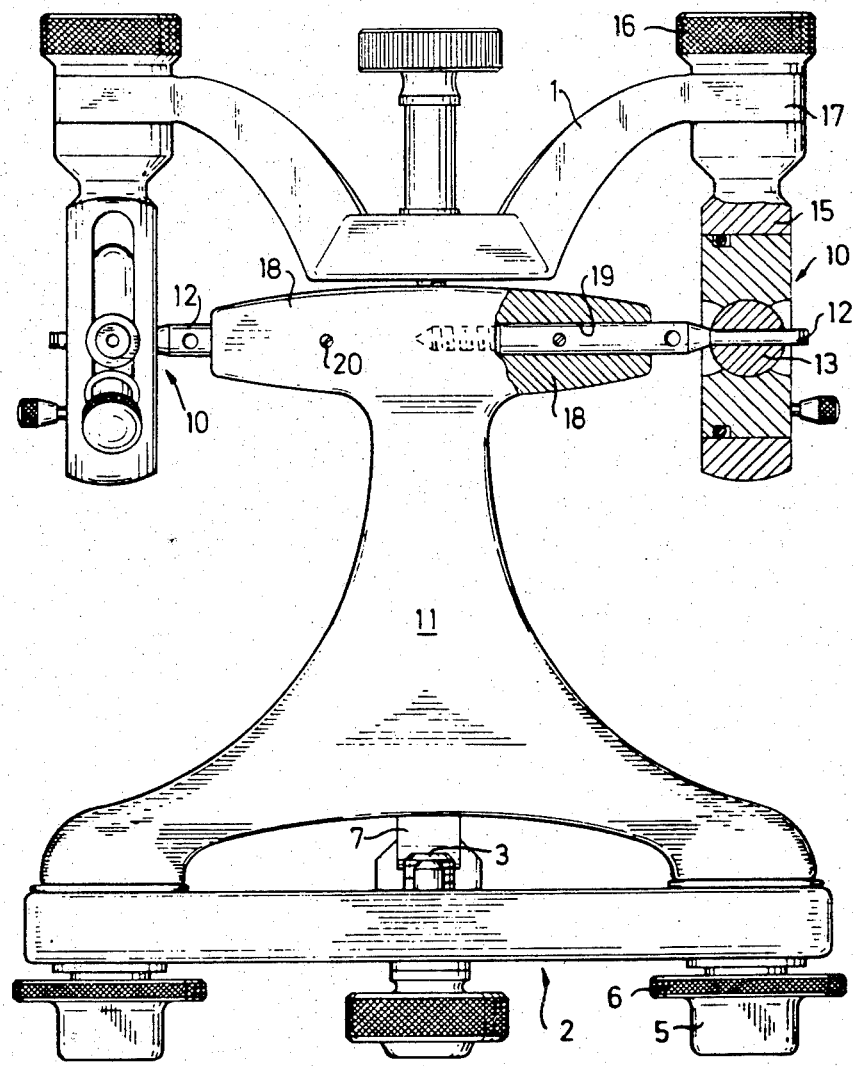
Figure 3:
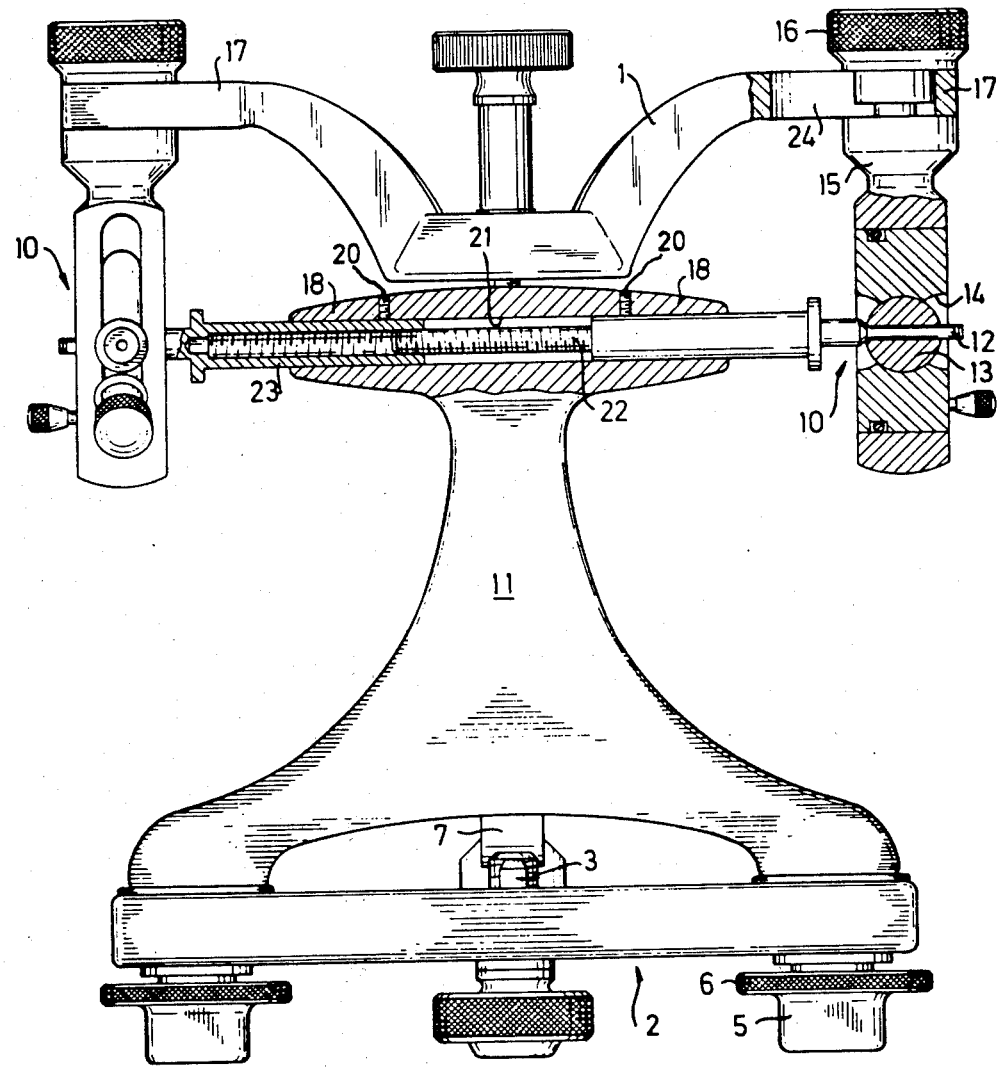

FIG. 1 shows a side view, cut-away in certain portions, of the first embodiment, FIG. 2 is a rear, partially cut-away view of this articulator as seen from the left in FIG. 1, and FIG. 3 is a rear, partially cut-away view, corresponding to FIG. 2, of the second articulator.

As can be seen from the drawings, articulators made according to the invention comprise two principal members 1,2. In both of the embodiments shown here, one 1 of the members forms the upper member of the articulator, while the other 2 forms its base or frame. The upper member 1 has approximately the shape of a T when viewed from above, while the base 2 has the form of a triangular or Y-shaped plate. The lower member or base 2 and the upper member 1 are provided centrally on their sides facing each other with fastening means in the form of known screws 3 and guide pins for anchoring models (not shown) of the patient's upper and lower sets of teeth.

On the bottom of the base 2, at every corner there is a foot 5 which is threaded into the base and is provided with a knurled portion 6, so that by screwing it in and out of the base it can serve as a levelling means. The top side of the base is also provided with a setting means 7 which cooperates with a measuring pin 8, extending downwards from the free end of the upper member. This pin together with the setting means 7 do not require any more detailed description here since both are previously known and described in, for example, U.S. Pat. No. 2,603,869.

The upper member 1 has on its top side an upwardly extending rod 9 which serves as a support for the upper member when it is swung completely back, i.e. swung back 180°, so that the free end of the rod 9 rests against the surface of the table on which the articulator is placed. More specifically, the articulators shown here according to the invention can be folded or swung out by virtue of the fact that their upper members 1 are pivotable in relation to the lower members or bases 2 with the aid of two condylar mechanisms which simulate the jaw joint movements of the patient and resemble ball and socket joints. They are of a known type which is marketed by AB Dentatus, Hägersten, Sweden, and therefore need not be described in more detail here.

According to the invention, one of the two principal members in an articulator made according to the invention is to support the other, and for this purpose it has a single slender arm or post. In both of the articulators shown here according to the invention, it is the lower members or bases 2 which support the upper members 1, and for this purpose the bases 2 are equipped with a vertical slender arm or post 11, which carries at its end towards the upper member the condylar shafts 12 which are included in the known condylar mechanisms, and condylar balls 13 displaceable on said shafts. The upper member 1 in both embodiments carries the condylar tracks 14 of these mechanisms. Said tracks 14 are adjustably and lockably mounted in annular holders 15, which in turn are fixed by means of set screws 16 at both ends of the laterally extending portion 17 of the T-shaped upper member 1.

In both of the embodiments shown here for an articulator according to the invention, the single slender arm or post 11 has a shape resembling an upside-down double candle holder with a long, slender mid-section. At the top towards the upper member 1, this arm or post 11 is provided with portions 18 extending on either side. Inside these portions, in the embodiment shown in FIGS. 1 and 2, there are two bores 19 which are collinear but pointing in opposite directions, a condylar shaft 12 being arranged in each bore and extending in either direction from the arm or post 11. The inner ends of the condylar shafts are threaded to engage corresponding threads in the interior of the two bores, at the same time as there are lock screws 20 for locking the shafts in said bores.

In the embodiment shown in FIG. 3, there is a common bore 21 for the two condylar shafts 12 which is open on both sides of the post 11 and extending through the two portions 18, protruding on either side, of the end of the post towards the upper member 1. The condylar shafts in this bore can be displaced and locked in the bore both individually and together, and parts 22 and 23 are threaded into each other. For locking, there are lock screws 20 in this embodiment as well.

If one desires to move one of the condylar shafts with its associated condylar ball, the associated lock screw 20 is first loosened, and the shaft can then be screwed out to the desired portion, and the lock or stop screw again be tightened. The same procedure applies to the condylar shaft on the opposite side. If one wishes to displace the two condylar shafts, connected in the middle, to different positions relative to the holder, this is done by loosening both of the lock screws 20 so that the two condylar shafts can be moved as a unit in one direction or the other.

In order to be able to cooperate with the two displaceable condylar shafts 12 in the embodiment shown in FIG. 3, and to achieve complete adjustability for the condylar mechanisms in the so-called Bennet plane, the condylar tracks 14 are both pivotable and lockable around two perpendicular axes, and are adjustable with regard to the distance between them, by virtue of the fact that the holders 15 for them are arranged displaceable on the upper member 1 transversely to the same. More specifically, this displaceability is achieved by slots 24 being arranged in portions extending transversely in this member. The condylar track holders 15 are lockable in these slots with their set screws 16.

The invention is not limited to the two embodiments described here and shown in the drawings. Rather, it can be modified in many ways within the scope of the claims.

What I claim is:

1. In an articulator for use in making dentures or parts thereof, which comprises two principal members (1,2), provided with anchoring means (3) for carrying models of the upper and lower rows of teeth, said members (1,2) being pivotable in relation to each other by means of two condylar mechanisms (10), which simulate the movements of the jaw joint, and one of said members (2) supporting the other (1), for which purpose said one member (2) has a single slender arm or post (11); the improvement in which said arm or post (11) at its end toward the other principal member (1) carries condylar shafts (12), that are included in said condylar mechanisms (10), condylar balls (13) which are displacable on said shafts (12), the other said member (1) carrying condylar tracks (14), and said single arm or post (11) having two collinear but oppositely directed apertures (19) at its end toward said other principal member (1), in which apertures (19) said condylar shafts (12) are arranged extending in either direction from said arm or post (11).

2. Articulator according to claim 1, in which the single arm or post (11) has a bore (21) extending between the two oppositely directed apertures (19).

3. Articulator according to claim 2, in which said condylar shafts (12) are displaceable and lockable in said bore (21) both individually and together, portions (22,23) of said shafts (12) located within the bore being threaded into each other.

4. Articulator according to claim 1, 2 or 3, in which the condylar tracks (14) are pivotable and lockable around two perpendicular axes and are also adjustable with respect to the spacing between them by holders (15) for said tracks laterally displaceable (16,24) on said other principal member (1) relative to said other member and lockable in relation to said other member.

5. Articulator according to claim 1, in which the principal member (2) provided with a single slender arm or post (11) forms the base or stand of the articulator, while the principal member (1) supported by said member (2) forms the upper member of the articulator.

* * * * *